United States Patent
Trombley

(10) Patent No.: US 9,938,075 B2
(45) Date of Patent: Apr. 10, 2018

(54) BEVERAGE CARTRIDGE CONTAINING PHARMACEUTICAL ACTIVES

(71) Applicant: The Procter & Gamble Company, Cincinnati, OH (US)

(72) Inventor: Kurt Franklin Trombley, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 255 days.

(21) Appl. No.: 14/554,122

(22) Filed: Nov. 26, 2014

(65) Prior Publication Data
US 2016/0145037 A1    May 26, 2016

(51) Int. Cl.
| | | |
|---|---|---|
| *A47J 31/00* | (2006.01) | |
| *A47J 31/40* | (2006.01) | |
| *B65D 65/40* | (2006.01) | |
| *B65D 85/804* | (2006.01) | |
| *B65D 50/00* | (2006.01) | |

(Continued)

(52) U.S. Cl.
CPC ............ *B65D 85/8046* (2013.01); *A61J 1/00* (2013.01); *A61J 1/1431* (2015.05); *A61K 31/135* (2013.01); *A61K 31/138* (2013.01); *A61K 31/167* (2013.01); *A61K 45/06* (2013.01); *B65D 25/04* (2013.01); *B65D 50/00* (2013.01);
(Continued)

(58) Field of Classification Search
CPC .............. B65D 75/366; B65D 75/367; B65D 85/8043; B65D 25/02; B65D 2215/00; B65D 2577/2075; B65D 2577/2091; A47J 31/24; A47J 31/401; A47J 31/3676; A47J 31/368; A47J 31/369; A47J 31/3695; A47J 31/40; A47J 31/0668; A47J 31/0673; A47J 31/0678; A47J 31/4464; A47J 31/4496; A23F 5/262; A23F 5/243; A61J 1/035; A61K 9/0095
USPC ...... 206/359.1, 0.5, 222; 220/524.1; 99/295; 426/77, 115, 112, 474
See application file for complete search history.

(56) References Cited

U.S. PATENT DOCUMENTS 3,498,525 A * 3/1970 Zinkgraf ................. B32B 15/08
229/123.1
4,211,326 A * 7/1980 Hein .................... B65D 75/327
206/461

(Continued)

FOREIGN PATENT DOCUMENTS

| EP | 2 154 101 A1 | 2/2010 |
| EP | 2 551 216 A1 | 1/2013 |

(Continued)

OTHER PUBLICATIONS

16 CFR Ch. II (1-1-12 Edition) § 1700.14 pp. 850-855.*
International Search Report and Written Opinion for PCT/US2014/067518, dated Feb. 27, 2015.

*Primary Examiner* — J. Gregory Pickett
*Assistant Examiner* — Gideon Weinerth
(74) *Attorney, Agent, or Firm* — Kelly L. McDow

(57) ABSTRACT

A child-resistant cartridge adapted to be used with an automatic brewing machine. The cartridge has a base and a lidding. The base can contain a pharmaceutical active. The lidding can be a multilayer laminate with an outer layer and an inner layer. The cartridge can be made out of tear resistant materials that are sufficient to prevent 70% of children from accessing the contents of three or more cartridges during a Child-Resistant Screening Test.

9 Claims, 6 Drawing Sheets

(51) Int. Cl.
  *B65D 25/04*    (2006.01)
  *B65D 51/00*    (2006.01)
  *A61K 31/167*   (2006.01)
  *A61K 31/138*   (2006.01)
  *A61J 1/00*     (2006.01)
  *A61J 1/14*     (2006.01)
  *A61K 45/06*    (2006.01)
  *A61K 31/135*   (2006.01)

(52) U.S. Cl.
  CPC ....... *B65D 51/002* (2013.01); *B65D 85/8043* (2013.01); *B65D 2215/00* (2013.01)

(56) References Cited

U.S. PATENT DOCUMENTS

| | | | | |
|---|---|---|---|---|
| 4,280,621 A * | 7/1981 | Tonrey | ............... | B65D 77/2064 206/459.5 |
| 4,286,011 A * | 8/1981 | Wong | ............... | B29C 55/08 428/212 |
| 4,311,741 A * | 1/1982 | Wong | ............... | B29C 55/08 220/260 |
| 4,874,656 A * | 10/1989 | Rantanen | ............... | B32B 27/08 206/524.2 |
| 5,325,765 A | 7/1994 | Sylvan et al. | | |
| 5,343,672 A * | 9/1994 | Kearney | ............... | A61J 1/035 53/440 |
| 5,840,189 A * | 11/1998 | Sylvan | ............... | B65D 85/8043 210/233 |
| 6,003,670 A * | 12/1999 | Beer | ............... | B32B 27/08 206/459.5 |
| 6,054,196 A * | 4/2000 | Koch | ............... | B32B 7/02 206/438 |
| D474,110 S | 5/2003 | Sweeney | | |
| D474,111 S | 5/2003 | Lazaris | | |
| 6,758,130 B2 * | 7/2004 | Sargent | ............... | A23F 3/14 426/115 |
| 7,041,351 B1 * | 5/2006 | Tse | ............... | B29C 47/0038 426/127 |
| 7,165,488 B2 | 1/2007 | Bragg et al. | | |
| 7,793,784 B2 * | 9/2010 | Nivala | ............... | B65D 75/327 206/1.5 |
| 7,919,171 B2 * | 4/2011 | Young | ............... | A61J 1/035 206/528 |
| 8,251,219 B1 * | 8/2012 | Lewis | ............... | A61J 1/035 206/528 |
| 8,361,527 B2 | 1/2013 | Winkler et al. | | |
| 8,479,921 B2 * | 7/2013 | Ingraham | ............... | A61J 1/035 206/528 |
| 9,468,584 B2 * | 10/2016 | Riis | ............... | B65D 65/40 |
| 2003/0005826 A1 * | 1/2003 | Sargent | ............... | A23F 3/14 99/279 |
| 2003/0108714 A1 * | 6/2003 | Razeti | ............... | B32B 7/12 428/138 |
| 2004/0045443 A1 | 3/2004 | Beaulieu et al. | | |
| 2005/0051478 A1 | 3/2005 | Basil et al. | | |
| 2005/0058788 A1 * | 3/2005 | Dent | ............... | B32B 15/08 428/35.2 |
| 2005/0260366 A1 * | 11/2005 | Magnusson | ............... | A23L 3/10 428/34.2 |
| 2005/0266122 A1 * | 12/2005 | Franceschi | ........ | B65D 81/3216 426/77 |
| 2005/0276942 A1 * | 12/2005 | Somani | ............... | B32B 27/08 428/35.7 |
| 2005/0284789 A1 * | 12/2005 | Carespodi | ............... | B32B 15/08 206/461 |
| 2006/0134388 A1 * | 6/2006 | Miller | ............... | D04H 3/14 428/174 |
| 2006/0278558 A1 * | 12/2006 | Nivala | ............... | B65D 75/327 206/538 |
| 2007/0224379 A1 * | 9/2007 | Stevenson | ............... | B32B 15/08 428/40.1 |
| 2007/0241552 A1 * | 10/2007 | Watson | ............... | B65D 75/367 283/81 |
| 2008/0245698 A1 * | 10/2008 | Young | ............... | A61J 1/035 206/531 |
| 2010/0247714 A1 | 3/2009 | Sylvan et al. | | |
| 2009/0317650 A1 * | 12/2009 | Yang | ............... | B32B 27/08 428/523 |
| 2010/0028495 A1 | 2/2010 | Laurence et al. | | |
| 2010/0121290 A1 * | 5/2010 | Rasmussen | ............... | A61F 5/441 604/333 |
| 2010/0154647 A1 * | 6/2010 | Skalski | ............... | A47J 31/0668 99/290 |
| 2011/0049003 A1 * | 3/2011 | Bellamah | ............... | B32B 15/08 206/531 |
| 2011/0151075 A1 | 6/2011 | Peterson | | |
| 2011/0262589 A1 * | 10/2011 | Safarik | ............... | A61J 1/035 426/5 |
| 2012/0097602 A1 | 4/2012 | Tedford | | |
| 2012/0111761 A1 * | 5/2012 | Sack | ............... | B65D 75/327 206/531 |
| 2012/0241449 A1 * | 9/2012 | Frischmann | ............... | B32B 7/02 220/200 |
| 2013/0129870 A1 | 5/2013 | Novak et al. | | |
| 2013/0209622 A1 | 8/2013 | Fountain et al. | | |
| 2013/0216824 A1 * | 8/2013 | Wade | ............... | B32B 7/12 428/332 |
| 2013/0270176 A1 | 10/2013 | Schreiber | | |
| 2013/0291737 A1 * | 11/2013 | Sims | ............... | A47J 31/407 99/281 |
| 2013/0306511 A1 * | 11/2013 | Branyon | ............... | B65B 61/025 206/469 |
| 2013/0341237 A1 * | 12/2013 | Krumme | ............... | B65D 75/5805 206/530 |
| 2014/0116906 A1 * | 5/2014 | Trombley | ............... | A61J 1/067 206/438 |
| 2014/0161936 A1 * | 6/2014 | Trombetta | ............... | B65D 85/816 426/77 |
| 2014/0208691 A1 * | 7/2014 | Ballering | ............... | B65D 77/30 53/432 |
| 2014/0272016 A1 * | 9/2014 | Nowak | ............... | B65D 85/8043 426/112 |
| 2014/0342059 A1 * | 11/2014 | Trombetta | ........ | B65D 85/8043 426/115 |
| 2014/0356484 A1 * | 12/2014 | Capitani | ............... | B65D 85/8043 426/77 |
| 2014/0370181 A1 * | 12/2014 | Young | ............... | A23F 5/02 426/595 |
| 2015/0017293 A1 * | 1/2015 | Carr | ............... | A47J 31/3623 426/232 |
| 2015/0056341 A1 * | 2/2015 | Trombetta | ........ | B65D 85/8043 426/115 |
| 2015/0096920 A1 * | 4/2015 | Trombley | ............... | B65D 75/36 206/531 |
| 2015/0166257 A1 * | 6/2015 | Trombetta | ............... | B65D 5/4204 426/87 |
| 2015/0239652 A1 * | 8/2015 | Trombetta | ........ | B65D 85/8043 426/115 |
| 2015/0298439 A1 * | 10/2015 | Osborn | ............... | B32B 27/08 206/531 |
| 2015/0314955 A1 * | 11/2015 | Savage | ............... | B65D 85/8046 426/115 |
| 2015/0368018 A1 * | 12/2015 | Broedsgaard | ........ | B65B 51/24 206/461 |
| 2016/0128903 A1 * | 5/2016 | Uetake | ............... | A61J 1/035 206/531 |
| 2017/0347825 A1 * | 12/2017 | Walter | ............... | A47J 31/0615 |
| 2018/0016091 A1 * | 1/2018 | Paige | ............... | B65D 85/8043 |

FOREIGN PATENT DOCUMENTS

WO    WO 2013/144838 A1    10/2013
WO    WO 2014/127467 A1    8/2014

* cited by examiner

BEVERAGE CARTRIDGE CONTAINING PHARMACEUTICAL ACTIVES

FIELD OF THE INVENTION

The present invention is related to a beverage cartridge and more particularly, a cartridge that is adapted to make beverages containing pharmaceutical actives.

BACKGROUND OF THE INVENTION

Currently, there are a number of cartridges for use in automatic brewing machines that make a single serving of a beverage product, such as coffee or tea. However, current cartridges are not suitable for use with pharmaceutical actives because the actives are sensitive to environmental conditions, such as humidity and oxygen, and the actives can degrade in current cartridges. Furthermore, the Consumer Product Safety Commission (CPSC) requires the primary package is child-resistant if the cartridge contains certain active ingredients, such as acetaminophen and diphenhydramine.

As such, there remains a need for a cartridge which is adapted for use in an automatic brewing machine that is both child-resistant and provides a barrier from environmental conditions to provide long term stability for pharmaceutical actives.

SUMMARY OF THE INVENTION

A child-resistant cartridge adapted to fit an automatic brewing machine comprising: (a) a base wherein the base contains a pharmaceutical active; and (b) a lidding wherein the lidding comprises a multilayer laminate comprising an outer layer and an inner layer; wherein the cartridge is made of tear resistant materials sufficient to prevent 70% of children from accessing the contents of five or more cartridges during a Child-Resistant Screening Test.

A child-resistant multi-layer laminate lidding adapted for a cartridge comprising: (a) an outer layer; and (b) an inner layer; wherein the lidding is made of tear resistant materials sufficient to prevent 70% of children from accessing the contents of five or more cartridges by puncturing the lidding during a Child-Resistant Screening Test and wherein the lidding is penetrable by a needle or other penetrator of an automatic brewing machine.

A child-resistant cartridge adapted to fit an automatic brewing machine comprising: (a) a base wherein the base contains a pharmaceutical active; and (b) a lidding; wherein the cartridge is made of tear resistant materials sufficient to prevent 70% of children from accessing the contents of five or more cartridges during a Child-Resistant Screening Test.

DETAILED DESCRIPTION OF THE INVENTION

Figure 1:
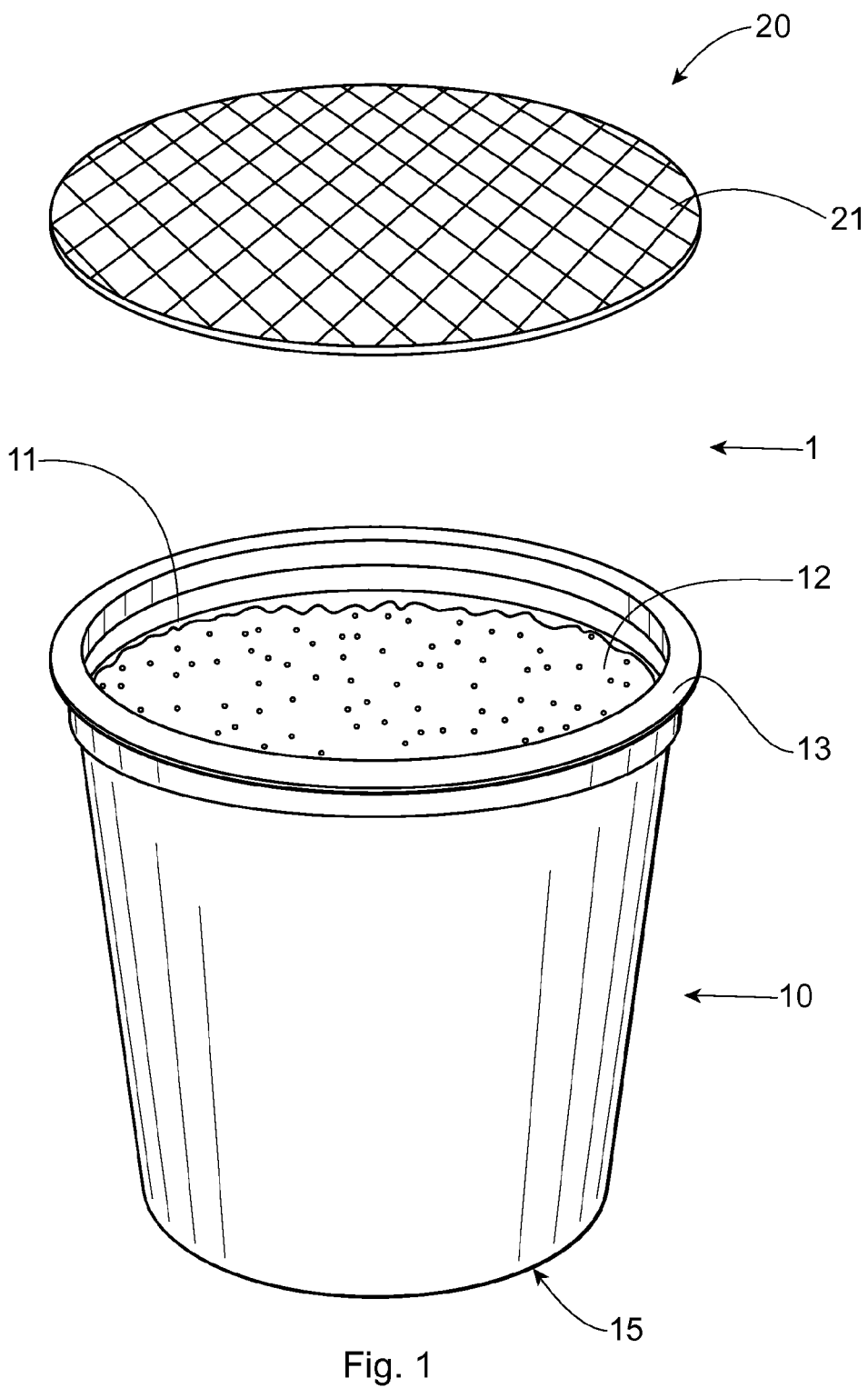
FIG. 1 is a three-dimensional exploded view of a beverage cartridge.

Many consumers enjoy drinking hot or cold beverages with pharmaceutical actives. A convenient and easy way to make a single serving of a hot or cold beverage is to use an automatic brewing machine with a cartridge. However, the current cartridges are not adapted to be used with pharmaceutical actives for two reasons. First, the current cartridge does not provide a sufficient barrier to environmental conditions to prevent degradation. Second, the current cartridges are not child-resistant. It has been observed that children are able to open the current cartridges with their teeth and then using their fingers to peel off the lidding to access the contents or by applying pressure to the lidding with their thumb to puncture the lidding. Furthermore, once a child figured out how to open one cartridge, he was able to quickly open additional cartridges.

The cartridges of the present invention can provide a sufficient barrier from environmental conditions including humidity and gases, including oxygen, and can be child-resistant. The structure and/or material(s) of the base and/or the lidding can provide long term stability for the pharmaceutical actives and/or child-resistance. The cartridge can have a base and a lidding structure. In one example, the base can be a multi-layer laminate, which can include polychlorotrifluoroethylene (PCTFE), an adhesive, and polyethylene terephthalate with a glycol modifier (PETG). In another example, the lidding can be a multi-layer laminate structure that can comprise aluminum foil, adhesive, and a plastic. The base and/or the lidding can be tear resistant. Furthermore, while being child-resistant, the bottom of the base and/or the lidding can still be penetrable by a needle or penetrator of the automatic brewing machine.

The cartridge can meet the definition of child-resistant under the U.S. Poison Prevention Packaging Act of 1970 (16 C.F.R. § 1700.14). Specifically, the cartridges can meet the definition of F=3 according to the Child-Resistant Testing as described herein. In another example, the cartridge can meet the definition of F=1 according to the Child-Resistant Testing, in another example F=2, in another example F=4, in another example F=5, and in another example F=6. In one example, the cartridge alone meets the definition of child-resistant without the secondary packaging.

The cartridge can be adapted for use in an automatic machine such as a single serving automatic brewing machine. Some of these machines can have a penetrator or needle that can penetrate the lidding and then provide a flow of water, frequently hot water, through the hole in the lidding, while a second penetrator or needle pushes through the bottom of the base to receive the outflow of the beverage and dispense it into a cup or container. Even though the base and the lidding layer are child resistant, in some examples, they can be penetrated by a penetrator or needle of a brewing machine. In another example, the child-resistant and/or barrier features do not interfere with normal operation of the automatic brewing machine.

As used herein, "active" or "pharmaceutical active" includes all compounds and compositions that can be used to treat and/or prevent illness and/or provide overall health and wellness benefits in mammals, particularly humans. Non-limiting examples of particularly useful actives include over-the-counter (OTC) actives, behind the counter actives, and prescription actives, vitamins, minerals, plant-derived materials, energy boosting materials, probiotics, fiber, prebiotics, and combinations thereof.

As used herein, "child-resistant" means a cartridge or other packaging that is designed or constructed to be significantly difficult for young children to open or obtain a toxic or harmful amount of the substance contained therein within a reasonable time and not difficult for normal adults to use properly, but does not mean packaging which all such children cannot open or obtain a toxic or harmful amount within a reasonable time.

As used herein, "dissolve" refers to passing into solution.

As used herein, "disintegrate" refers to breaking up into small parts.

As used herein, "permanently joined" refers to configurations in which a first element is secured to a second element such that the elements generally cannot be separated from one another without at least partially destroying one or both of the elements.

As used herein, "primary packaging" refers a packaging component that is or may be in direct contact with the dosage form.

As used herein, "releasably joined" refers to configurations in which a first element is secured to a second element, such that the first element and the second element can be separated with no or minimal damage to the first and second elements.

As used herein, "tear resistant" means capable of experiencing a reasonable level of stress and/or deformation without experiencing a significant loss of integrity. Stress and/or deformation can be applied by a number of movements including, but not limited to, biting, pulling, pealing, poking, pushing and/or jabbing at the cartridge. In one example, any of these movements can be performed by a child, and tear resistant refers to a material that is capable of experiencing a reasonable level of stress and/or deformation without experiencing a significant loss of integrity when undergoing forces that can be applied by a child. In one example, the child is six years or younger, in another example five years or younger, in another example four years or younger, in another example three or younger, in another example two or younger, and in another example 18 months or younger. In one example, even though the cartridge is tear resistant, it can still be punctured with the needle or penetrator of an automatic brewing machine.

As used herein, the term "treat" or "treating" includes preventing, alleviating, ameliorating, inhibiting, or mitigating one or more health conditions in a mammal, in particular a human and in one example an adult human. Non-limiting examples of health conditions can include respiratory conditions.

As used herein, the articles "a" and "an" are understood to mean one or more of the material that is claimed or described, for example, "an active" or "a compartment".

Figure 2:
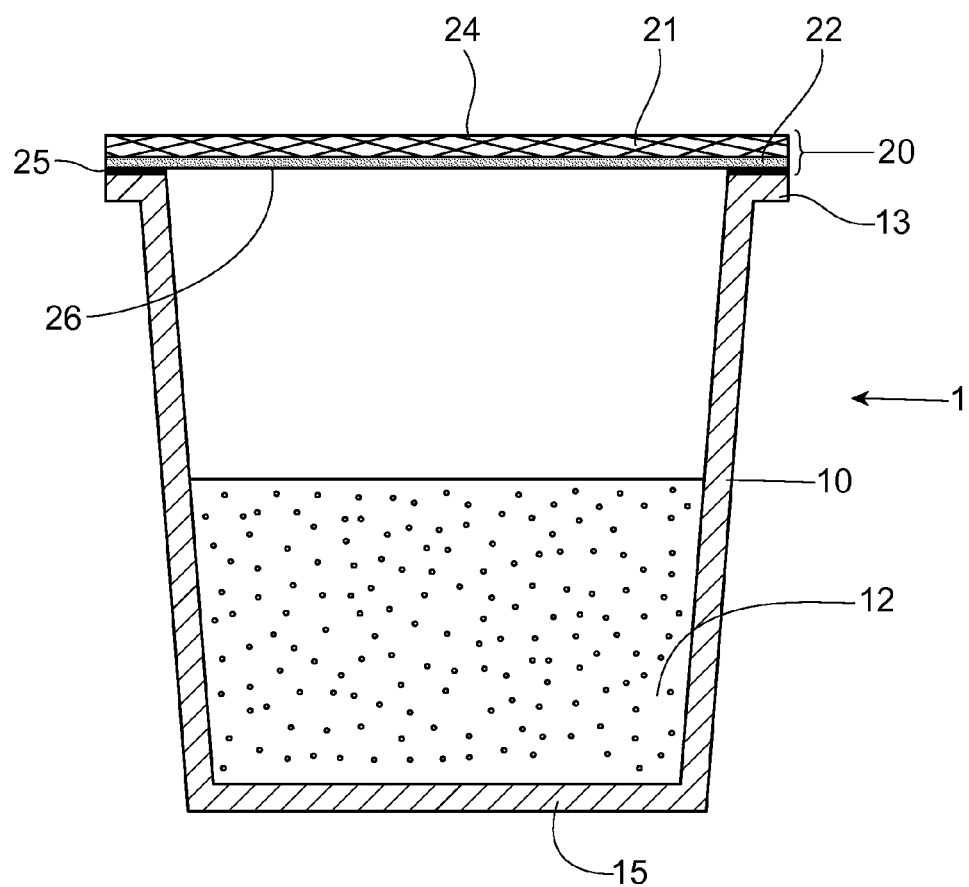
FIG. 2 is a side sectional view of a beverage cartridge of FIG. 1.

FIG. 1 shows an exploded view of cartridge 1 and FIG. 2 shows a side sectional view of cartridge 1. Cartridge 1 includes base 10 and lidding 20. Base 10 includes opening 11 and outwardly facing rim 13. Base 10 can have the shape of a cup, cylinder, bowl, or an inverted truncated cone. Base 10 can include component 12, which can include an active and/or an excipient. In one example, the component can be a powder. Bottom 15 of base 10 can be penetrable by a penetrator or needle during use.

With reference to FIG. 2, inner surface 26 of lidding 20 can be permanently joined to rim 13 of base 10 at seal 25. The lidding can be joined to the base by any suitable method. In one example, the lidding has a coating that is heat activated, causing it to attach to the rim of the base when exposed to heat. In another example, the lidding can be attached using ultrasonic frequency and in another example the lidding can be attached using induction heating. Alternatively, the lidding can be attached with a contact adhesive.

Lidding 20 can be a child-resistant laminate with outer layer 21 and inner layer 22. Outer layer 21 can provide the child-resistance and can be tear resistant while still be penetrable by a needle or other penetrator of an automatic brewing machine. In one example, outer layer 21 can contain reinforced strands 24, which can provide additional child resistance. Reinforced strands 24 can form a mesh across lidding 20 and in one example, the mesh can be open at the location where the lidding is intended to be punctured by a needle or penetrator. In one example, the reinforced strands can be embedded in the child-resistant laminate. In another example, the reinforced strands are underneath the outer layer. In another example, the reinforced strands can be underneath the inner layer. In another example, the reinforced strands can be between the outer layer and the inner layer. In another example, the reinforced strands can be embedded in the outer layer and/or the inner layer. The reinforced strands can be made of any suitable material including nylon, polypropylene, fiberglass, and combinations thereof.

Inner layer 22 can reduce the amount of gasses, including oxygen, from entering cartridge 1. Inner layer 22 can be made out of any suitable material and in one example, inner layer 22 can be made out of aluminum foil. Inner layer 22 can be opaque which can provide additional child-resistance. In another example, inner layer 22 can also include ink. In one example, outer layer 21 and inner layer 22 are permanently joined by an adhesive.

The lidding can be both child-resistant and provide an adequate barrier from gasses and humidity, while still being penetrable by a needle or other penetrator of an automatic brewing machine. In one example, the lidding is a laminate. The laminate can have any number of layers. In one example the laminate has at least two layers, in another example at least three layers, in another example at least four layers, and in another example at least five layers. In another example, the lidding can be only one layer. In one example, one or more layers of the lidding can be opaque and in another example one or more layers of the lidding can be transparent.

Figure 3:
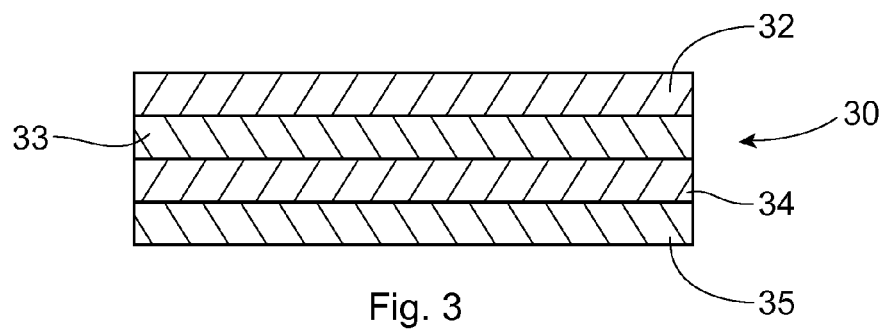
FIG. 3 is a side sectional view of a lidding for a beverage cartridge.

FIG. 3 is an example of a side sectional view of lidding 30 for a beverage cartridge. Lidding 30 can comprise outer layer 32, second layer 33, third layer 34, and inner layer 35. In one example, outer layer 32 can comprise polyethylene terephthalate (PET), second layer 33 can comprise orientated polyamide (OPA), third layer 34 can comprise aluminum, and inner layer 35 can comprise polyethylene vinyl acetate (PE-EVA). In another example, inner layer 35 can comprise linear low-density polyethylene (LLDPE). In one example, each layer is attached to an adjacent layer with an adhesive. In another example, ink is between the outer layer and the second layer. In another example, ink is printed on the outer layer. In another example, a heat seal coating partially or entirely covers the inner layer.

Figure 4A:
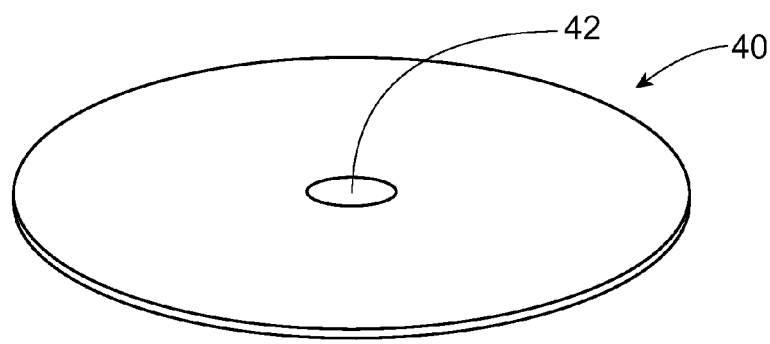
FIG. 4A is a lidding for a beverage cartridge.
Figure 4B:
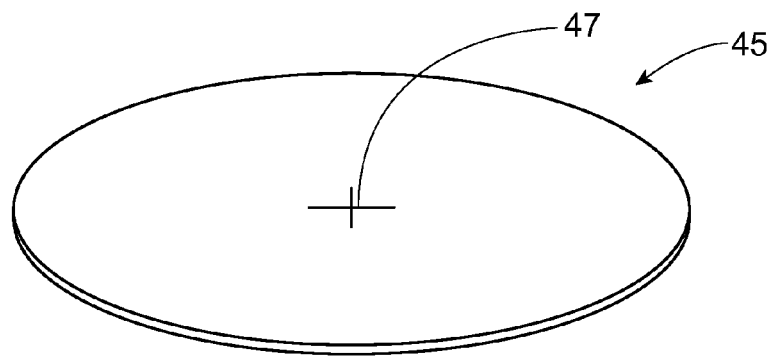
FIG. 4B is a lidding for a beverage cartridge.

FIGS. 4A and 4B are examples of liddings with weakened areas. The weakened area can be in the region that is intended to be punctured by a needle or other penetrator of an automatic brewing machine. This weakened area can allow the lidding to be child resistant while still allowing the lid to be penetrated by a needle or penetrator. The weakened area can extend partially or completely through one or more layers of the laminate lidding. In one example, the weakened area is on the outer layer of the lidding. In another example, the weakened area is not on the outer layer of the lidding because a child could see the weakened area and gain access or pick and peel at an edge of the weakened area. In one example, the weakened area does not penetrate the inner layer. In another example, the weakened area only penetrates or partially penetrates the outer layer. In one example, the weakened can be small enough so it is difficult for a child to use it to access the cartridge contents. In one example, the weakened area is from about 1 mm to about 12 mm at its widest point, in another example from about 2 mm to about 10 mm, and in another example from about 3 mm to about 8 mm.

FIG. 4A is an example of lidding 40 with a weakened area, hole 42. The hole can be any suitable shape. Non-limiting examples of shapes can include a circle, square, diamond, rectangle, triangle, star, cross, oval, and combinations thereof.

FIG. 4B is an example of lidding 45 with a weakened area, scored portion 47. Scored portion 47 can be in any of the shapes listed above, as well as an "x", cross-hatching, multiple dots, and combinations thereof.

Figure 5:
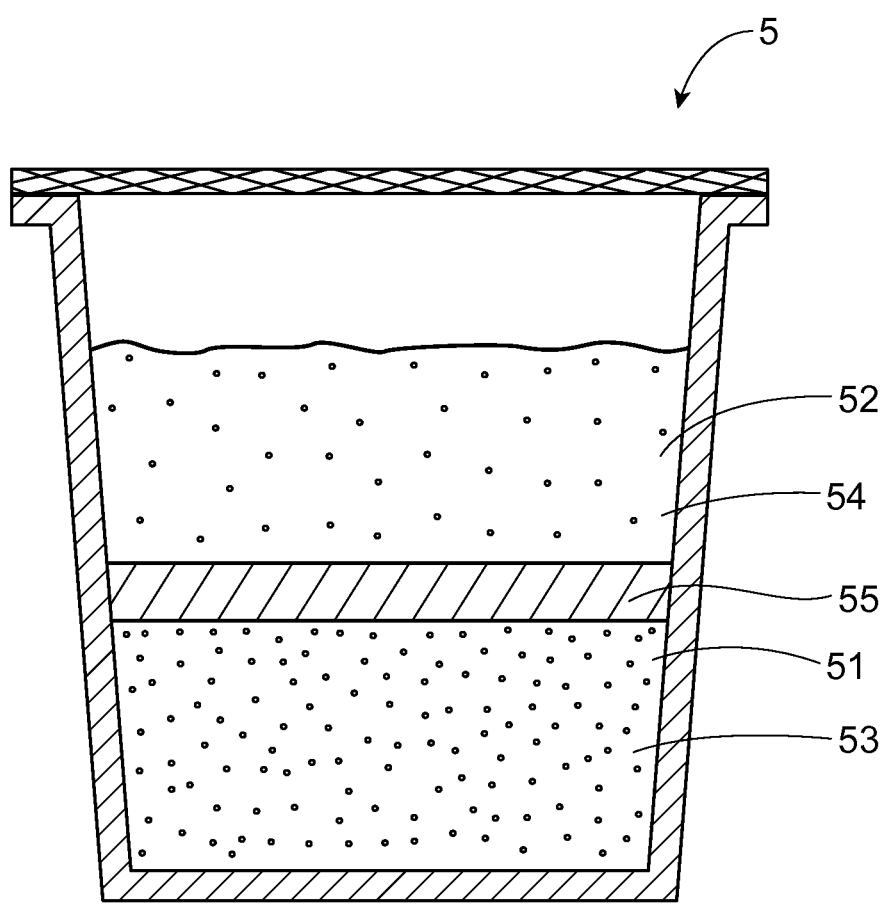
FIG. 5 is a side sectional view of a beverage cartridge with two compartments.

FIG. 5 is an example of a side sectional view of beverage cartridge 5 with more than one compartment. For some components it could be advantageous to separate some of the ingredients until immediately before they are consumed. In one example, the actives and/or excipients are incompatible and separating them prolongs the stability of the components. In another example, the components are in different states, for example one component is a solid and the other is a liquid. In another example, one compartment contains a component with an active and another compartment contains a component with a flavor, which could allow for more robust flavor delivery, particularly if the flavor was a liquid.

In FIG. 5, beverage cartridge 5 has first compartment 51 containing first component 53 and second compartment 52 containing second component 54. First compartment 51 and second compartment 52 are separated by divider 55.

The divider can be any suitable material. In one example the divider partially or completely dissolves or partially or completely disintegrates, when exposed to hot or cold water. In another example, the divider can be a mesh or woven material that separates the components when they are solid but when the components dissolve in water, the solution can travel through the mesh or woven material. In another example, the divider can be punctured with the needle or penetrator from the automatic brewing machine. When the divider is punctured, water and the second component can flow from the second compartment to the first compartment.

The beverage cartridge can have multiple compartments. In one example, the beverage cartridge can have at least two compartments, in another example at least three compartments, and in another example at least four compartments. The compartments can extend in any direction including horizontally across the cartridge, vertically from the bottom of the base to the lidding, diagonally, or combinations thereof.

Figure 6:
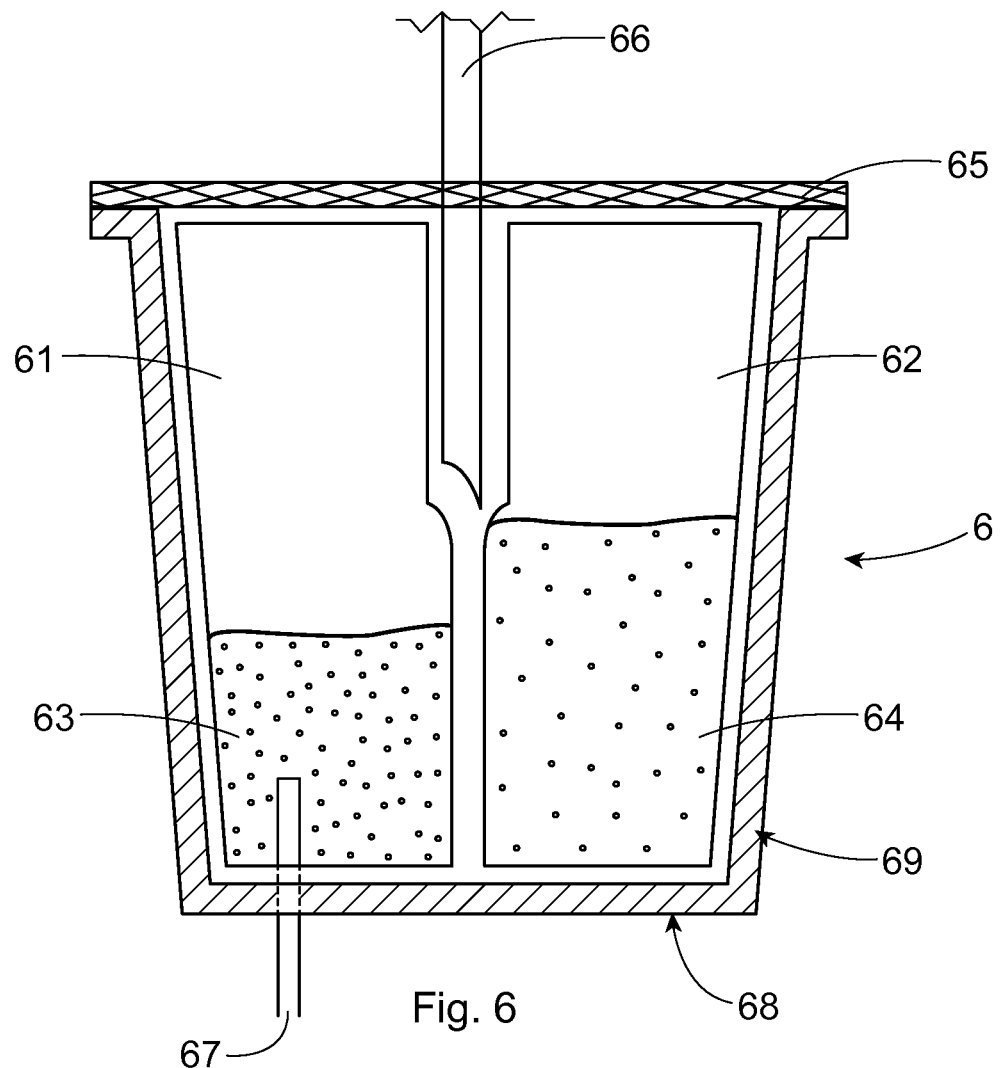
FIG. 6 is an example of a side sectional view of a beverage cartridge with two chambers.

FIG. 6 is an example of side sectional view of beverage cartridge 6 with multiple chambers. Cartridge 6 has first chamber 61 containing first component 63 and second chamber 62 containing second component 64. The chambers not only can keep the components separate until just before use but they can also allow the user to select which actives she wants in her beverage.

In one example, the automatic brewing machine can have an upper needle 66, which punctures lidding 65, approximately in the center, and does not puncture first chamber 61 or second chamber 62. Simultaneously, lower needle 67 punctures the bottom 68 of base 69 and chamber 63. Lower needle 67 does not puncture the middle of base 67, instead it punctures off center. Thus by arranging cartridge 6 with a particular orientation in the brewing machine, one chamber could be broken, while the other chamber remains intact. In one example, the chambers can be made of a frangible material and/or can be pre-scored so when the lower needle punctures the chamber it cracks or breaks completely in two or more parts. Non-limiting examples of frangible materials can include starch based films, water soluble modified cellulose films such as hydroxyethyl cellulose, ethyl vinyl acetate films, and combinations thereof. When the brewing begins, water will flow out the upper needle and flow around the intact chamber, while combining with the components of the broken chamber and making a beverage with the desired components.

For instance, the first chamber may contain an active to treat aches and pains, such as acetaminophen or ibuprofen, and the second chamber may contain an active to treat cough, such as dextromethorphan. If the consumer does not have a cough she can position the cartridge in the automatic beverage brewer such that only the chamber that has the actives for aches and pains is penetrated by the bottom needle. However, if the consumer wants both actives she can brew twice, puncturing both chambers.

In another example, the chamber can contain different flavors allowing the user to select a flavor of her beverage.

In another example, the upper needle can puncture both chambers. The lower needle punctures only one chamber and liquid from the upper needle can flow into both chambers but the beverage will only be able to flow out of the chamber punctured by lower needle. Thus, the consumer can make a beverage with the desired components.

The cartridge can have any suitable number of chambers. In one example, the cartridge can have at least two chambers, in another example at least three chambers, and in another example at least four chambers. In one example, the cartridge could have a single chamber that could allow the consumer to make a beverage with just the component outside the chamber or with both components.

In another example, the chambers can be used to separate incompatible components.

Figure 7:
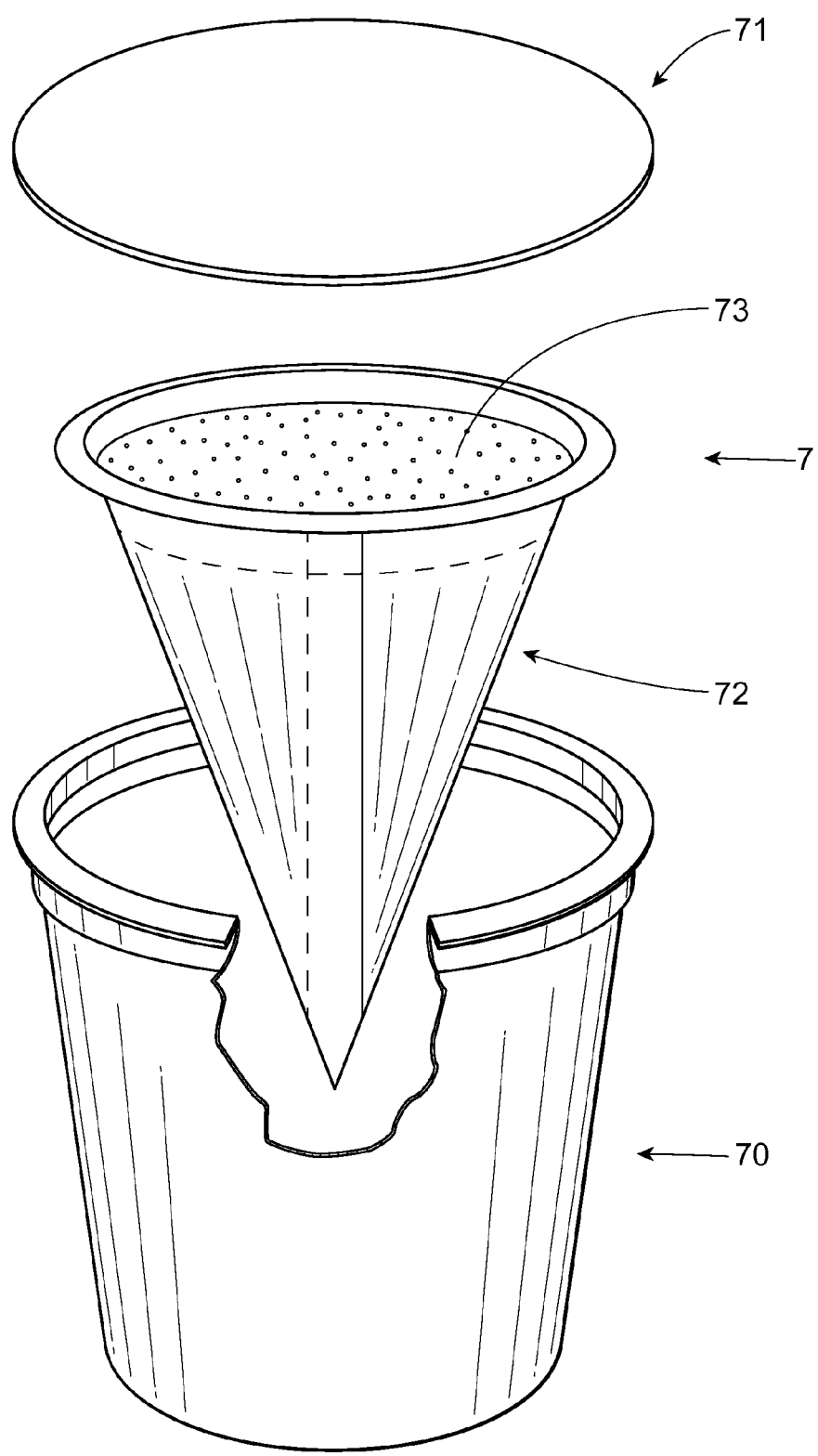
FIG. 7 is an example three-dimensional exploded view of a beverage cartridge with a filter.

FIG. 7 is an example of a cartridge 7 with a base 70, lidding 71, and a filter 72. Filter 72 contains component 73. The filter can be used when brewing a drink, such as coffee or tea. The water will seep through the filter and extract the essence of the components and the solid particles will be retained in the filter. In one example, the actives and/or other excipients can dissolve into the water as it passes through the filter. In one example, the cartridge with a filter can be used to brew coffee or tea containing actives.

In one example, the cartridge does not contain a filter.

In another example, at least one of the ingredients are packaged in a separate container and added by the consumer, or person preparing the beverage for the consumer, before or after their beverage is brewed by the automatic brewing machine. In one example the ingredient can be a flavor and in another example the ingredient can contain one or more actives. In one example, the separate container can be a sachet. In one example, the separate container can contain a liquid. In another example the separate container can contain a solid, where the solid can be a powder, nonpareils, capsule, tablet, or combinations thereof. In another example, the consumer uses the automatic brewing system to puncture the top of the cartridge but before brewing the beverage the consumer reopens the machine and adds the separately packaged ingredient to the cartridge through the hole made by the automatic brewing machine and then recloses the machine and brews their beverage.

The base can be made of any suitable material(s) that provide the desired barrier properties and child-resistance and can still be penetrated by the needle or penetrator of the automatic brewing machine. Non-limiting examples of materials that can be incorporated into the laminate material of the base can include high-density polyethylene (HDPE), cyclic olefin copolymers (COC), biaxally orientated polyamide (OPA), polypropylene (PP), polyester (PET), amorphous polyethylene terephthalate (APET), polyvinyl chloride (PVC), polyethylene (PE), aluminum foil, and combinations thereof. In another example the laminate can include a polyvinylidene chloride coating and in another example the laminate can include ethylvinyl alcohol (EVOH). In one example, the base can be transparent and in another example the base can be opaque.

In one example, the base can be a laminate made from polychlorotrifluoroethene (PCTFE), an optional adhesive, and polyethylene terephthalate glycol (PETG). In one example, the PETG can be from about 25 μm to about 1.5 mm thick, in another example from about 50 μm to about 1 mm, in another example from about 100 μm to about 500 μm, and in another example from about 200 μm to about 300 μm. In another example, the PCTFE can be from about 10 μm to about 250 μm, in another example from about 25 μm to about 150 μm, in another example from about 30 μm to about 100 μm, and in another example from about 40 μm to about 75 μm.

In one example, the base can be a laminate with an inner layer and an outer layer. In one example, the inner layer can be EVOH, or another material that is difficult for a child to puncture or tear. The inner layer and the outer layer of the base can be releasably joined. When the child tries to open the container, for instance by puncturing, tearing, or biting, the inner layer can separate from the outer layer. This separation can slow the child down, which can give a parent or caregiver more time to intervene and prevent the child from accessing cartridges. This separation may also make the child feel like they are making progress getting the package open, when in reality delaminating these two layers is not contributing to gaining access to the component, since the child cannot break through the inner and/or outer layer.

In one example, the maximum thickness of the base material can be greater than the maximum thickness of current pharmaceutical product barrier materials, such as cavities on a blister card, because the cartridge has dimensions larger than a typical pharmaceutical product enclosure. Using base material with a greater starting thickness provides for sufficient thickness when the base of the cartridge is formed because the material is stretched by a greater degree towards the bottom of the cartridge base.

Current lidding can be removed by children with a combination of biting and scratching. Thus, the lidding can be tear resistant. In one example, the lidding is a multi-layer laminate. Non-limiting examples of materials that can be incorporated into the laminate material of the lidding can include aluminum foil, PCTFE, EVOH, HDPE, OPA, COC, PP, PET, APET, PVC, PE, and combinations thereof.

For both the laminate in the lidding layer and the base, the layers of the laminate can be affixed by an adhesive layer, which can comprise a polyolefin material like low density polyethylene (LDPE).

In one example, the laminate can have an outer layer, a second layer, and an inner layer. The outer layer can be PET, the second layer can be foil, and the inner layer can be LLDPE.

In one example the outer layer or PET layer can be from about 5 μm to about 40 μm thick, in another example from about 10 μm to about 35 μm thick, in another example from about 15 μm to about 30 μm thick, and in another example from about 20 μm to about 25 μm thick. In one example the outer layer or PET layer can be greater than about 8 μm, in another example greater than about 11 μm, in another example greater than about 16 μm, in another example greater than about 20 μm, and in another example greater than about 22 μm.

In another example, the second layer or foil layer can be from about 3 μm to about 30 μm, in another example from about 8 μm to about 25 μm thick, and in another example from about 15 μm to about 22 μm thick. In another example the second layer or foil layer can be greater than about 5 μm thick, in another example greater than about 8 μm thick, in another example greater than about 12 μm thick, in another example greater than about 15 μm thick, and in another example greater than about 17 μm thick.

In another example, the inner layer or LLDPE layer can be from about 10 μm to about 40 μm thick, in another example from about 15 μm to about 35 μm thick, in another example from about 20 μm to about 30 μm thick, and in another example from about 22 μm to about 27 μm thick. In another example, the inner layer or LLDPE layer can be greater than about 8 μm thick, in another example greater than about 13 μm thick, in another example greater than about 18 μm thick, in another example greater than about 20 μm thick, in another example greater than about 22 μm thick, and in another example greater than 24 μm thick.

The base, lidding, and/or cartridge can provide an effective barrier. In one example, the base, lidding, and/or cartridge can have a final moisture vapor transmission rate of about $2 \times 10^{-5}$ to about $2 \times 10^{-3}$ g/cartridge/day, in another example from about $1 \times 10^{-4}$ to about $6 \times 10^{-4}$ g/cartridge/day, and in another example from about $2 \times 10^{-4}$ to about $3 \times 10^{-4}$ g/cartridge/day, as determined by the United States Pharmacopeial (USP) <671> (Aug. 1, 2013). Follow Method 1 of the procedure for Single-Unit Containers and Unit-Dose Containers for Capsules and Tablets.

The cartridge can provide long term stability to the pharmaceutical actives. In one example, the pharmaceutical active in the cartridge have a shelf life of at least about 1 year, in another example at least about 18 months, in another example at least about 2 years, and in another example at least about 2.5 years. As used herein, "shelf life" refers to the time period during which a drug product is expected to remain within the approved shelf life specification, provided that it is stored under the conditions defined on the container label. The conditions under which shelf life testing is conducted, the specific measurements and the minimum requirements for usable, fit for consumption or saleable can be set by governmental or regulatory bodies and can be published in guidance documents such as the United States Pharmacopeial (USP) or ICH Harmonised Tripartite Guideline *Stability Testing of New Drug Substances and Products Q1A(R2)*, Step 4, of the version published Feb. 6, 2003.

In one example, the pharmaceutical active is at least about 90% of label for at least 1 year, in another example for at least about 1.5 years, in another example for at least about 2 years, and in another example for at least about 3 years. In another example the pharmaceutical active is at least about 95% of label for at least 1 year, alternatively at least about 1.5 years, alternatively at least about 2 years. The cartridge may provide long term stability by maintaining the pharmaceutical active above about 80% or label for at least about 1 year, alternatively at least about 1.5 years, alternatively at least 2 years.

The cartridges can be in secondary packaging. In one example, the secondary package can be a standard paperboard box that contains from about 1 to about 12 cartridges, and in another example from about 3 to about 6 cartridges. In another example, the secondary package can be child-resistant. In one example, the secondary package can contribute to the overall child-resistance of the cartridge. In another example the secondary package can be an F=1 child-resistant package, in another example an F=2 child-resistant package, and in another example an F=3 child-resistant package. In another example, each cartridge is individually packaged in a secondary package. In another example, the secondary packaging can provide additional barrier properties to help prolong stability of the components.

In one example, the cartridge can be used with an automatic brewing machine and can be adapted to fit in an automatic brewing machine. In another example, the cartridge can be used without an automatic brewing machine.

In one example, the cartridges are disposable which means that the cartridge can be disposed of or discarded after a limited number of uses. In one example, the cartridge can be used five or fewer times, in another example three or fewer times, in another example two or fewer times, and in another example the cartridge is used only one time. In another example, the cartridge can be reused and can be refilled with a component containing an active and/or an excipient.

The component can include both one or more actives and/or one or more excipients. The component can be in any suitable form including, but not limited to, a powder, a liquid, a gel, or a tablet. Non-limiting example of excipients can include flavors, sweeteners, disintegrants, fillers, colors, lubricants, glidants, sorbents, preservatives, sensates, and combinations thereof. In one example, the component is a powder that dissolves as the water passes through the cartridge. In another example, the component is a concentrated liquid that can be diluted when the water passes through the cartridge. In yet another example, the component is only partially dissolved or extracted to make the beverage.

The cartridge can contain one or more actives. In one example, the beverage containing actives can be consumed by adults and children 12 years and over. In another example, the beverage containing actives can be intended to be consumed by children, often under the supervision of an adult.

The actives can treat a variety of symptoms including, but not limited to, symptoms from cold, flu, or allergies. Non-limiting examples of actives can include decongestants, expectorants, antihistamines, antitussives, pain relievers, and combinations thereof.

In one example, the cartridge can provide multi-symptom relief of cold and/or flu symptoms and can be intended for use at night. The cartridge can deliver about 650 mg acetaminophen, about 30 mg dextromethorphan HBr, about 10 mg of phenylephrine, about 30 to about 60 mg of pseudoephedrine, and/or about 12.5 mg doxylamine succinate during a single brew cycle.

In some examples, how much active is delivered, does not necessarily mean that the cartridge contains this amount of active. The cartridge will likely contain more active than what is delivered to the user since in some examples, not all of the active will be transferred from the cartridge to the beverage. Furthermore, according to government regulations, such as the USP, the delivered amount of active can be within 10% of the monographed amount.

In another example, the cartridge can help relieve occasional sleeplessness and/or can help reduce the time to fall asleep if you have difficulty falling asleep. The cartridge can provide about 50 mg diphenhydramine HCl or about 25 mg of doxylamine succinate.

In another example, the cartridge can help the user treat allergy symptoms. The cartridge can deliver about 25 mg to about 50 mg diphenhydramine HCl, about 10 mg loratadine, about 650 mg to about 1000 mg acetaminophen, about 7.5 mg to about 12.5 mg doxylamine, and/or about 10 mg phenylephrine.

In another example, the cartridges can be sold in combination with other products, in particular products containing over-the-counter actives or vitamins and/or minerals. In one example, the cartridge can contain actives intended for nighttime relief of cold and/or flu symptoms and the cartridge can be packaged or otherwise sold in combination with actives intended for daytime relief of cold and/or flu symptoms such as acetaminophen, dextromethorphan, and phenylephrine. In another example, the cartridge can contain vitamins, for instance a tea containing vitamins, and it can be packaged or otherwise sold in combination with over-the-counter actives, for instance actives containing daytime and/or nighttime relief of cold and/or flu symptoms. The over-the-counter actives can be any dosage form including, but not limited to, a liquid, solid dosage forms such as liquicaps or tablets, or a cartridge.

The automatic brewing machine can dispense an entire dose of active as determined by the monograph. Thus, the active can quickly dissolve or can be extracted into water as it is being brewed. In one example, the cartridge can contain more than the monographed dosage of the active in order to ensure that the correct dosage is in the consumer's cup. The beverage can be any volume. In one example the beverage is from about 100 mL to about 500 mL, in another example from about 125 mL to about 250 mL, in another example from about 130 mL to about 250 mL, and in another example about 150 mL to about 200 mL. In one example, the beverage is about 6 fluid ounces (177.41 mL) and in another example the beverage is about 8 fluid ounces (236.59 mL).

In one example, following each use the automatic brewing machine can be rinsed with water or otherwise cleaned to remove residual actives and/or excipients. For example, a brewing cycle can be conducted by the consumer without a cartridge in the machine. In one example, the automatic brewing machine can be cleaned with water. In another example, the automatic brewing machine can be cleaned with a cleaning agent, for instance a cleaning agent comprising vinegar. Some consumers may also want to clean the brewing machine before brewing the beverage.

In one example, the cartridge can be child-resistant and can be given a rating that is referred to as the F value. The F Value refers to the number of unit doses to which access is considered a test failure. The number following the "F" refers to the number of unit doses that may produce serious personal injury or serious illness based on a 25-pound (11.4 kg) child.

The Child-Resistant Test is a standardized test and can be found in 16 C.F.R. § 1700 Poison Prevention Packaging. In one example, the child-resistant package is an F=1 package, in another example an F=2 package, in yet another example an F=3 package, in another example an F=4 package, and in yet another example an F=5 package.

In one example about 80% or more of the children in the child resistance test cannot access the contents of 5 cartridges or fewer, in another example about 70% or more of the children cannot the contents of 5 cartridges or fewer, in another example about 60% or more of the children cannot access the contents of 5 cartridges or fewer. In another example about 80% or more of the children in the child resistance test cannot access the contents of 4 cartridges or fewer, in another example about 70% or more of the children cannot access the contents of 4 cartridges or fewer, in another example about 60% or more of the children cannot access the contents of 4 cartridges or fewer. In another example, about 80% or more of the children in the child resistance test cannot access the contents of 3 cartridges or fewer, in another example about 70% or more of the children cannot access the contents of 3 cartridges or fewer, in another example about 60% or more of the children cannot access the contents of 3 cartridges or fewer. In another example, about 80% or more of the children in the child resistance test cannot access the contents of 2 cartridges or fewer, in another example about 70% or more of the children cannot access the contents of 2 cartridges or fewer, in another example about 60% or more of the children cannot access the contents of 2 cartridges or fewer.

Test Methods

Child-Resistant Testing

The child-resistant testing can be conducted according to the Code of Federal Regulations Title 16: Part 1700.

Child-Resistant Screening Test

The Child-Resistant Screening Test can be conducted as follows:

For the Child-Resistant Screening Test the children are between 42-51 months of age. Both boys and girls are selected in approximately even numbers.

A test failure is defined as any child who gains access to the cartridge contents. For the following experiment, the test was a failure if any child accessed the contents of three or more cartridges during the full 10 minutes of testing. As used herein, "gained access to" means that the actives have been removed or can be removed in whole or in part. In the case of a cartridge, the active can be removed if any amount of active can spill out of the cartridge if it is inverted. If a cartridge or package is breached and the contents are not removed but could be removed, this is still considered access.

The children are tested two at a time. The two children are escorted to the test area and are seated so there is no physical barrier between the children and the tester. The tester will talk to the children to make them at ease. The children are not given the impression that they are in a race or a contest, they are not offered a reward, and they are not told that the test is a game or that it is fun. To begin the test the tester shall hand the children identical cartridges and say "Please try and open this for me." If the child refuses to participate after the test has started, the tester shall reassure the child and gently encourage the child to try. If the child continues to refuse, the tester shall ask the child to hold the cartridge in his/her lap until the other child is finished. This pair of children shall not be eliminated from the results unless the refusing child disrupts the participation of the other child.

Each child will be given 5 minutes to open his/her cartridge. The tester shall minimize conversations with the children as long as they continue to attempt to open their packages. The tester shall not discourage the children verbally or with facial expressions. If a child gets frustrated or bored and stops trying to open his/her cartridge, the tester shall reassure the child and gently encourage the child to keep trying. The children should be allowed freedom of movement to work on their cartridges as long as the tester can watch both children (e.g. they can stand up, get down on the floor, or bang or pry the package). The children shall be allowed to talk to each other about opening the cartridges and shall be allowed to watch each other try to open packages. If the child opens his/her cartridge, the tester shall say, "Thank you," and take the opened cartridge from the child and give the child another unopened cartridge.

At the end of the 5-minute period, the tester shall ask the children to put their cartridges down and then shall demonstrate how to open the cartridge. This demonstration is done by performing a demonstration of how to use the cartridge in the machine, a Keurig® K75 Platinum Edition brewer. The children shall not be allowed to continue to try to open their cartridges during the demonstration period. The tester shall say, "watch me use this package." Once the tester gets the children's full attention, the tester shall hold the demo package approximately two feet from the children and open the package at a normal speed as if the tester were going to use the contents. There shall be no exaggerated opening movements. The tester shall not discuss or describe how to open the package. After opening the package, the tester shall show the children the package.

Then, the children are given a second five-minute period to try and open their cartridges. The tester begins the five minute period by saying, "now you try to open your packages." If both children have not used their teeth to try to open their packages during the first 5 minutes, the tester shall say immediately before or soon after beginning the second 5-minute period, "You can use your teeth if you want to." This is the only statement that the tester shall make about using teeth. The test shall continue for another five minutes or until both children have opened their packages, whichever comes first.

Example 1

Example 1 shows the results from the Child-Resistant Screening Test. The procedures for the Child-Resistant Screening Test were followed as described above. The trial used Swiss Miss K-Cups® (purchased at Keurig.com, on Oct. 25, 2013, lot number 6696 PL120, expiration date Jan. 17, 2015). Table 1, below, shows how many cartridges were opened and how long it took to open each one. Table 2, describes how each of the cartridges that were opened was accessed.

TABLE 1

| | Gender | Age (mo) | First 5 min test period Time to open cartridge (min) | | | | | | Second 5 min test period Time to open cartridge (min) | | | | | |
|---|---|---|---|---|---|---|---|---|---|---|---|---|---|---|
| | | | 1 | 2 | 3 | 4 | 5 | 6 | 1 | 2 | 3 | 4 | 5 | 6 |
| 1 | Male | 42 | | | | | | | | | | | | |
| 2 | Female | 43 | | | | | | | | | | | | |
| 3 | Female | 43 | | | | | | | | | | | | |
| 4 | Male | 45 | | | | | | | | | | | | |
| 5 | Female | 45 | | | | | | | | | | | | |
| 6 | Male | 46 | | | | | | | | | | | | |
| 7* | Female | 45 | 1:42 | 2:54 | 3:22 | 3:42 | 4:20 | 4:31 | 6:10 | | | | | |
| 8 | Female | 49 | 4:30 | | | | | | 6:29 | 6:43 | 7:04 | 7:14 | 7:24 | |
| 9 | Male | 51 | | | | | | | 6:00 | 6:25 | 6:31 | 6:50 | 6:58 | 7:05 |
| 10 | Female | 49 | | | | | | | | | | | | |
| 11 | Male | 51 | | | | | | | | | | | | |
| 12* | Male | 50 | | | | | | | 5:58 | 6:57 | 7:38 | 9:12 | | |
| 13 | Male | 46 | | | | | | | | | | | | |
| 14 | Female | 42 | | | | | | | | | | | | |
| 15 | Female | 43 | | | | | | | | | | | | |
| 16 | Female | 43 | | | | | | | | | | | | |
| 17 | Male | 48 | | | | | | | 5:32 | 6:01 | 6:31 | 6:39 | 6:59 | 7:21 |
| 18 | Male | 50 | | | | | | | 5:21 | 5:46 | 6:01 | 6:13 | 6:32 | 7:16 |
| 19 | Female | 48 | | | | | | | 7:49 | 8:06 | 8:32 | 8:57 | 9:59 | 10:12 |
| 20 | Male | 43 | | | | | | | 7:00 | 7:36 | 8:07 | 8:32 | 9:19 | 10:00 |
| 21 | Male | 50 | | | | | | | | | | | | |

*Child was given a cartridge that had a reinforced top for second five minute test period.
The top was reinforced with packing tape that was reinforced with fiber. The tape was adhered over the lidding of the Swiss Miss K-Cup ® and a hotplate was used to further bond the tape to the lidding.

TABLE 2

| | Gender | Age (mo) | Description of how cartridges were opened during the first 5 min test period | Description of how cartridges were opened during the second 5 min test period |
|---|---|---|---|---|
| 7* | Female | 45 | Child used teeth. | Child was given a cartridge with reinforced tape for the second five minutes. Child peeled re-enforced tape and then used teeth. |
| 8 | Female | 49 | Child used teeth. | Child used teeth to puncture foil top and then used fingers to tear the foil. |
| 9 | Male | 51 | n/a | Child punctured with finger to open the first cartridge and then used his teeth to open the five others. |
| 12* | Male | 50 | n/a | Child was given a cartridge with reinforced tape for the second five minutes. Child peeled the the reinforced tape and then used teeth. |
| 17 | Male | 48 | n/a | Child used teeth to puncture foil top and then used fingers to tear the foil. |
| 18 | Male | 50 | n/a | Child used teeth to puncture foil top and then used fingers to tear the foil. |
| 19 | Female | 48 | n/a | Child punctured foil top with thumb. |
| 20 | Male | 43 | n/a | Child used teeth to puncture foil top and then used fingers to tear the foil. |

The Child-Resistance Screening Test with the Swiss Miss K-Cups® had a 65% pass rate. The container passed if the child opened two or fewer cartridges. This is not an acceptable level of child-resistance for beverage products that contain pharmaceutical products, especially products containing acetaminophen or diphenhydramine. Almost all of the children who accessed the contents, used their teeth to puncture the lidding. Thus, in order to make a child resistant cartridge it can be important to have a lidding that cannot be punctured or torn by biting. One child opened the package by applying steady pressure with his thumb to puncture the foil lidding. Thus, the lidding can also be made child resistant if it is not susceptible to being opened by pressing.

It is also interesting to note that after the children saw the demonstration and were told they could use their teeth, many more children gained access to the contents of the cartridge. Also, if a child was able to open one cartridge, he or she was generally able to open the remaining cartridges very quickly. Therefore, in order to make the cartridge child-resistant, it may be necessary to make the cartridge tear resistant.

Although the cartridges which were reinforced with packing tape were not child resistant, it did take the children longer to access the contents of these cartridges. Thus, if the heat seal was stronger, the child-resistant properties of the package may be improved.

Although the two children who received cartridges with reinforced tops were able to access the contents, they were not able to access the contents by biting or otherwise puncturing the reinforced tape. Instead, they were able to separate the reinforced tape from the K-Cup® lidding by pealing. Therefore, if the packing tape was more securely adhered to the lidding, for instance in a laminate structure, a sufficient level of child-resistance could be achieved.

Example 2

Example 2 shows the results from the second Child-Resistant Screening Test utilizing laminate lidding structure believed to be superior to those tested in Example 1. The procedures for the Child-Resistant Screening Test were followed as described above. This example used the same base as Example 1; however the lidding had a different laminate structure. The laminate had an outer layer, a second layer, and an inner layer. The outer layer was 12 µm PET, the second layer was 9 µm foil, and the inner layer was 25 µm LLDPE. The outer layer was connected to the second layer with adhesive and the second layer was connected to the inner layer with adhesive. The cartridges were filled with Ovaltine® (batch number #401158801G). Table 3, below, shows how many cartridges were opened and how long it took to open each one. Table 4, describes the method used for each child who opened three or more cartridges during the Child-Resistant Screening Test. Age groups are as follows: A=42-44 months, B=45-48 months, and C=49-51 months old.

This Child-Resistance Screening Test with the laminate lidding of Example 2 had a 75% pass rate counting child #12 and a 80% pass rate if he was excluded. The container passed if the child opened three or fewer cartridges. 75% is not an acceptable level of child-resistance (80% is the minimum level of acceptance) for beverage products that contain pharmaceutical products, especially products containing acetaminophen or diphenhydramine. Almost all of the children who accessed the contents, used their teeth or fingers to puncture the lidding. Thus, in order to make a child resistant cartridge it can be important to have a lidding that cannot be punctured or torn by biting.

Example 3

Example 3 shows the results from the third Child-Resistant Screening Test utilizing new packaging component materials believed to be superior to those tested in Example 1 and Example 2. The procedures for the Child-Resistant Screening Test were followed as described above. The trial used the same base as Example 1; however the lidding had a different laminate structure. The laminate had an outer

TABLE 3

| | Gender | Age (group) | First 5 min test period Time to open cartridge (min) | | | | | | Second 5 min test period Time to open cartridge (min) | | | | | |
|---|---|---|---|---|---|---|---|---|---|---|---|---|---|---|
| | | | 1 | 2 | 3 | 4 | 5 | 6 | 1 | 2 | 3 | 4 | 5 | 6 |
| 1 | Female | A | | | | | | | | | | | | |
| 2 | Male | B | | | | | | | | | | | | |
| 3 | Male | A | | | | | | | | | | | | |
| 4 | Male | B | 4:40 | | | | | | | | | | | |
| 5 | Female | B | | | | | | | | | | | | |
| 6 | Female | B | | | | | | | | | | | | |
| 7 | Female | C | | | | | | | 6:00 | 8:02 | | | | |
| 8 | Male | C | | | | | | | | | | | | |
| 9 | Female | B | | | | | | | 6:01 | 7:12 | 7:16 | | | |
| 10 | Female | C | | | | | | | 7:16 | 7:45 | 8:22 | | | |
| 11 | Male | C | 1:40 | 1:54 | 2:31 | | | | | | | | | |
| 12** | Male | C | | | | | | | 7:34 | 8:01 | 9:05 | | | |
| 13 | Female | C | | | | | | | | | | | | |
| 14 | Male | C | | | | | | | | | | | | |
| 15 | Female | C | | | | | | | | | | | | |
| 16 | Female | C | | | | | | | | | | | | |
| 17 | Female | B | | | | | | | | | | | | |
| 18 | Female | A | | | | | | | | | | | | |
| 19 | Male | A | | | | | | | | | | | | |
| 20 | Female | A | | | | | | | 7:20 | 8:43 | 9:21 | | | |

**Child found a way to access the product using an artifact of the method used to make the prototype samples for testing. It is believed, that normal manufacturing would not allow this access method to be as successful.

TABLE 4

| | Gender | Age (group) | Description of how cartridges were opened |
|---|---|---|---|
| 9 | Female | B | Peeled lid, poked with thumbs/finger, struck against floor |
| 10 | Female | C | Peeled lid, struck against floor |
| 11 | Male | C | Poked hard with thumb/knuckle |
| 12** | Male | C | Peeled lid, crushed until plastic formed small hole, banged on package, poking at thin spot in plastic (artifact of prototyping) |
| 20 | Female | A | Peeled lid, used teeth after demo | layer, a second layer, and an inner layer. The outer layer was 23 µm PET, the second layer was 18 µm foil, and the inner layer was 25 µm LLDPE. The outer layer was connected to the second layer with adhesive and the second layer was connected to the inner layer with adhesive. The cartridges were filled with Ovaltine® (batch number #401158801G). Table 5, below, shows how many cartridges were opened and how long it took to open each one. Table 6, describes the method used for each child who opened three or more cartridges during the Child-Resistant Screening Test. Age groups are as follows: A=42-44 months, B=45-48 months, and C=49-51 months old.

TABLE 5

| | | First 5 min test period Time to open cartridge (min) | | | | | | Second 5 min test period Time to open cartridge (min) | | | | | |
|---|---|---|---|---|---|---|---|---|---|---|---|---|---|
| Gender | Age (group) | 1 | 2 | 3 | 4 | 5 | 6 | 1 | 2 | 3 | 4 | 5 | 6 |
| 1 Male | B | | | | | | | | | | | | |
| 2 Male | B | | | | | | | | | | | | |
| 3 Female | A | | | | | | | | | | | | |
| 4 Male | A | | | | | | | | | | | | |
| 5 Male | B | | | | | | | | | | | | |
| 6 Female | A | | | | | | | | | | | | |
| 7 Female | B | | | | | | | | | | | | |
| 8 Male | B | | | | | | | | | | | | |
| 9 Male | B | | | | | | | 6:27 | 6:53 | 7:02 | | | |
| 10 Female | B | | | | | | | 9:58 | | | | | |
| 11 Female | C | | | | | | | | | | | | |
| 12 Male | B | | | | | | | | | | | | |
| 13 Male | C | | | | | | | | | | | | |
| 14 Female | C | | | | | | | | | 7:58 | | | |
| 15 Male | C | | | | | | | | | | | | |
| 16 Female | C | 2:17 | 2:40 | 3:09 | | | | | | | | | |
| 17 Female | C | | | | | | | | | | | | |
| 18 Male | A | | | | | | | | | | | | |
| 19 Male | B | | | | | | | | | | | | |
| 20 Female | B | | | | | | | | | | | | |

TABLE 6

| Gender | Age (mo) | Description of how cartridges were opened |
|---|---|---|
| 9 Male | B | Peeled lid, used teeth after demo to access all three containers |
| 16 Female | C | No detail given except required very little effort |

This Child-Resistance Screening Test with the laminate lidding of Example 3 had a 90% pass rate. The container passed if the child opened three or fewer cartridges. 90% is an acceptable level of child-resistance (80% is the minimum level of acceptance) for beverage products which contain pharmaceutical products, especially products containing acetaminophen or diphenhydramine.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non-fiber containing child-resistant cartridge adapted to be used with an automatic brewing machine comprising:
   a. a base wherein the base contains a pharmaceutical active; and
   b. a lidding wherein the lidding comprises a multilayer laminate comprising a PET outer layer, a foil second layer and a LLDPE inner layer wherein the inner layer is adjacent to the base;
   wherein the cartridge prevents 90% of children from accessing the contents of three or more cartridges during a Child-Resistant Screening Test;
   wherein the outer layer is at least 23 µm thick, the second layer is at least 18 µm thick, and wherein the inner layer is at least 25 µm thick, said layers being bonded together with LDPE; and
   wherein the lidding does not contain a mesh reinforcement, and
   wherein the lidding comprises a weakened area whose widest point is from about 3 mm to about 8 mm, said weakened area is not on the outer layer of a needle or other penetrator of an automatic brewing machine.

2. The child-resistant cartridge of claim 1 wherein the cartridge comprises a final moisture vapor transmission rate of about $2 \times 10^{-5}$ to about $2 \times 10^{-3}$ grams of moisture per cartridge per day.

3. The child-resistant cartridge of claim 1 further comprising an excipient and wherein the excipient and the pharmaceutical active are a powder.

4. The child-resistant cartridge of claim 1 further comprising an excipient and wherein the excipient and the pharmaceutical active are a concentrated liquid.

5. The child-resistant cartridge of claim 1 wherein the base further comprises a first compartment containing the pharmaceutical active and a second compartment containing a second pharmaceutical active wherein the first compartment and the second compartment are separated by a divider.

6. The child-resistant cartridge of claim 5 wherein the divider is a mesh.

7. The child-resistant cartridge of claim 5 wherein the pharmaceutical active and the second pharmaceutical active are incompatible.

8. A child-resistant cartridge according to claim 1 wherein the pharmaceutical active comprises acetaminophen and wherein the cartridge can deliver about 650 mg of acetaminophen during a brew cycle.

9. The child-resistant cartridge of claim 1 wherein the cartridge contains a pharmaceutical active comprising diphenhydramine and optionally acetaminophen and wherein the cartridge can deliver about 50 mg of diphenhydramine during a brew cycle.

* * * * *

UNITED STATES PATENT AND TRADEMARK OFFICE
CERTIFICATE OF CORRECTION

PATENT NO.         : 9,938,075 B2
APPLICATION NO.    : 14/554122
DATED              : April 10, 2018
INVENTOR(S)        : Kurt Franklin Trombley Page 1 of 1

It is certified that error appears in the above-identified patent and that said Letters Patent is hereby corrected as shown below:

In the Claims

Column 18, Lines 44 – 47:
Please delete "wherein the lidding comprises a weakened area whose widest point is from about 3mm to about 8mm, said weakened area is not on the outer layer of a needle or other penetrator of an automatic brewing machine" and please insert the following --wherein the lidding comprises a weakened area whose widest point is from about 3mm to about 8mm, said weakened area is not on the outer layer of the lidding and is penetrable by a needle or other penetrator of an automatic brewing machine.--

Signed and Sealed this
Sixth Day of November, 2018

Andrei Iancu
*Director of the United States Patent and Trademark Office*